United States Patent [19]

Kolehmainen et al.

[11] 4,303,752

[45] Dec. 1, 1981

[54] SELECTIVE DETERMINATION OF NUCLEOTIDES IN VIABLE SOMATIC AND MICROBIAL CELLS

[76] Inventors: Seppo E. Kolehmainen, Rte. 2, Riveredge Dr., Box 66 X, Titusville, Fla. 32780; Veikko Tarkkanen, Postbus 31101, 6370 AC Schaesberg, Netherlands

[21] Appl. No.: 98,763

[22] Filed: Nov. 30, 1979

Related U.S. Application Data

[63] Continuation-in-part of Ser. No. 911,071, May 31, 1978, abandoned.

[30] Foreign Application Priority Data

May 31, 1977 [GB] United Kingdom ............... 22992/77

[51] Int. Cl.$^3$ .......................... C12Q 1/06; C12Q 1/66; C12Q 1/34
[52] U.S. Cl. .......................................... 435/8; 435/18; 435/29; 435/34; 435/820
[58] Field of Search ................... 435/6, 8, 29, 34, 181, 435/180; 426/18, 820

[56] References Cited

U.S. PATENT DOCUMENTS

| | | | |
|---|---|---|---|
| 3,645,852 | 2/1972 | Axen et al. ........................ | 435/181 |
| 3,745,090 | 7/1973 | Chappelle et al. .................. | 435/8 |
| 3,788,948 | 1/1974 | Kagedal et al. .................... | 435/180 |
| 3,930,956 | 1/1976 | Juni ................................ | 435/6 |
| 3,971,703 | 7/1976 | Picciolo et al. .................... | 435/8 |
| 4,014,745 | 3/1977 | Fletcher et al. .................... | 435/8 |
| 4,144,134 | 3/1979 | Chris Jr. .......................... | 435/8 X |

OTHER PUBLICATIONS

Reese et al., Surfactants as Stimulants of Enzyme Production By Microorganisms, Applied Microbiology, vol. 17, No. 2, 1969, (pp. 242-245).

*Primary Examiner*—David M. Naff

[57] ABSTRACT

A method is disclosed for measuring the concentration of nucleotides and the number of viable cells in a biological sample containing somatic and/or microbial cells by treatment of a sample of cells with surface active agents to selectively release the nucleotides without rupture of the cell membrane or walls, and measuring by means of a bioluminescent assay technique the concentration of nucleotides selectively released and thereby determining the number of viable cells in the sample.

18 Claims, 1 Drawing Figure

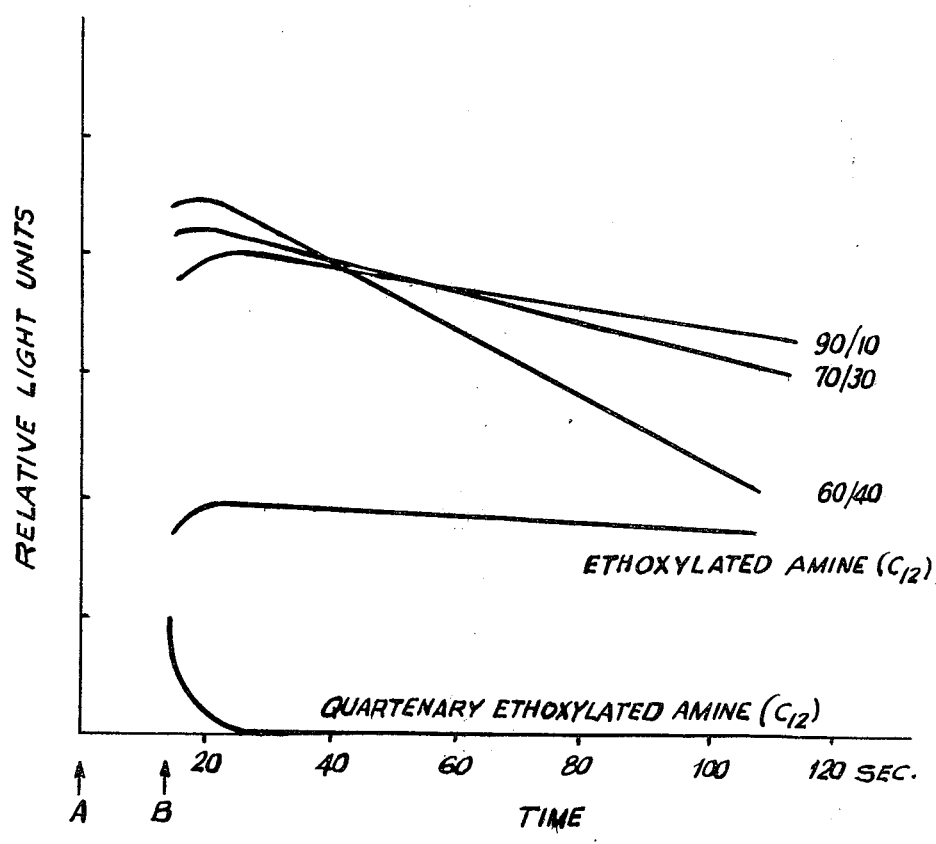

SELECTIVE DETERMINATION OF NUCLEOTIDES IN VIABLE SOMATIC AND MICROBIAL CELLS

This application is a continuation-in-part of Ser. No. 911,071, filed May 31, 1978, now abandoned.

BACKGROUND OF THE INVENTION

This invention relates to selective measurement of the number of different types of viable cells or their activity in a sample of cells through the utilization of surface active agents. This method is based on selective releasing of nucleotides from somatic cells and microbials cells, and subsequent measurement of nucleotides by bioluminescence.

Measurement of somatic (eucaryotic) and microbial cells is of great importance in medical laboratories, veterinary science, food hygiene, the fermentation industry and environmental sciences. Bacteria, yeasts and fungi are measured either by standard colony counting in a growth medium or by instruments, such as a microscope, turbidometer, nephelometer and the like. Somatic cells are counted with particle counters, such as an electro-optical particle counter and instruments based on detecting fluorescent particles, or indirect measurement based on the quantity of a metabolic product, or by microscopy. The methods require either complex, expensive equipment or are not accurate due to interference from non-cellular particles or non-somatic cells. Furthermore, most conventional methods do not make any distinction between dead and viable cells.

With conventional methods it has been difficult and time consuming to selectively determine different types of cells in samples containing both somatic and microbial cells. Conventional methods in microbiology have been so slow that it takes 24 to 72 hours to obtain the results. In clinical tests the results should be obtained as soon as possible in order to start proper treatment. In food hygiene it is as important to determine promptly the level of microbial contamination of raw materials and finished products, as in clinical samples, to protect the consumers and prevent spoilage of food. Therefore, rapid alternatives for colony counting have been looked for.

Firefly bioluminescent measurement of adenosine triphosphate (ATP) (see U.S. Pat. No. 3,745,090) is a rapid and sensitive method for determining the number of bacterial cells in a sample. In this method the quantity of measured ATP is converted to number of cells by dividing the quantity of ATP in the sample by the level of ATP per living cell. ATP level in a particular type of viable cell is relative constant. Similarly, the bioluminescent system of photobacteria has been used to measure bacterial cells by applying the level of assayed flavin mononucleotide (FMN) level in the sample to calculate the number of bacteria.

In order to determine the number of bacteria in foodstuffs and body fluids, such as milk, urine, blood, central spinal fluid, saliva and seminal fluid, ATP in somatic cells has to be eliminated quantitatively. Body fluids contain blood, epitelial, muscle and sperm cells, and the ATP level of these is higher than that of bacterial cells. Therefore, only a few somatic cells can cause a large error in the measurement of bacteria if somatic ATP is not eliminated prior to the microbial ATP assay. Likewise, the interference by the nucleotides from microbial cells has to be avoided when somatic cells are measured in samples containing both cell types. The utilization of bioluminescent assays has been limited by the lack of suitable simple and selective sample preparation methods for different types of cells.

Selective measurement of both somatic and microbial cells are needed in many fields of science, medicine, hygienic and industrial quality control. In these fields selective measurement of cells fall into three categories:
1. Measurement of somatic cells in the presence of microbial cells;
2. Measurement of microbial cells in the presence of somatic cells;
3. Measurement of total viable cells.

The present invention makes it possible to accomplish these measurements, rapidly, simply, and more accurately than with conventional methods. The principles and the different alternatives of utilization of the methods based on this invention are shown in the examples hereinafter described.

DESCRIPTION OF THE INVENTION

It is a known fact that surface active agents have been used to rupture (lyze) single cells in order to eliminate ATP from somatic cells (U.S. Pat. No. 3,745,090), but the above method has drawbacks which limit its applicability. Rupturing of the cell membrane allows enzymes to be released from somatic cells and they can cause interference in the later phases of the assay of nucleotides. The above mentioned patent suggests both non-ionic detergents (octyl phenoxy polyethoxyethanol, terpenoid saponins, steroid saponins, sulfosuccinate glycosides, and fatty acid esters of sorbitol anhydrides) and ionic detergents to be used to rupture somatic cells. Some of these, particularly the ionic surface active agents, affect the permeability of the microbial cell wall and membrane and release nucleotides (ATP, FMN and other small molecules) from microbial cells. As a result such surfactants cannot be used for selective rupturing of somatic cells prior to measurement of microbial ATP or other nucleotides. The present invention describes methods of applying specific surface active agents for selective release of nucleotides (purine and pyridine nucleotides, and PMN) either for somatic or microbial cells. This selective release of nucleotides is accomplished without releasing enzymes from cells and the assay of nucleotides can be made without interference from undesired enzymatic hydrolysis of assayed nucleotides.

Concentration of nucleotides is measured in metabolic studies, biochemistry, clinical chemistry and bioassays. About one third of the known 2000 enzymes use purine nucleotides (ATP, ADP, AMP GTP, GMP, ITP, etc.) and pyridine nucleotides (NAD, NADH, NADP, NADPH, CTP, UTP, etc.) as substrates. In conventional methods these substrates have been extracted from cells by destroying the cells by physical or chemical means and inactivating the enzymes in the cells by freezing, heating or with chemicals. In many conventional methods proteins have to be separated from the sample before the measurement of nucleotides. Such complicated manipulations can cause errors in the assay and they make the sample preparation laborious. The present invention makes the sample preparation simple, rapid and reproducible. When these methods are used in conjunction with bioluminescent assay of metabolites, the measurement is specific to ATP, FMN, NADH OR NADPH; whichever is meant to be measured. The samples need not be deproteinized nor the nucleotides separated by chromatography or liquid extraction techniques.

DESCRIPTION OF PREFERRED EMBODIMENT

Selective Measurement of Somatic and Microbial Cells

Sample Preparation

In the present invention the nucleotides are released from single cells in suspension or from mono- and bilayers of cells through the cell wall and cell membrane permeable by means of the action of surface active agents. Certain surface active agents change the permeability of the cell membrane by affecting the integrity of the lipid and phospholipid layer in the membrane. It is possible to select certain non-ionic surface active agents which do not lyze the somatic cell but make the cell membrane permeable to small-size molecules, such as purine and pyridine nucleotides. When the cell membrane is made permeable to small molecules, nucleotides diffuse out of the cells instantaneously, but enzymes and proteins having a large molecular size will not be able to penetrate the membrane and stay inside the cells. This allows a simple and rapid extraction of nucleotides from cells without having to inactivate enzymes in the cells. Released nucleotides in extracellular solution are stable for several minutes if the solution does not have endogenous enzymes or broken cells in high enough quantities to cause a rapid, undesired enzymatic hydrolysis of nucleotides in the solution. By selecting a non-ionic surfactant that does not lyze somatic cells but only changes the permeability of the membrane, does not affect microbial cell walls, and does not inhibit the bioluminescent reaction, it is possible to release nucleotides selectively from somatic cells for assaying by bioluminescent systems. However, microbial cells, such as bacteria, yeasts, fungi and slime molds have a cell wall that is resistant to chemical and environmental factors. The cell wall contains substances, such as muramic acid (a peptidoglycan) in bacteria, and chitinous substances in fungi which protect the more fragile cell membrane. Therefore, it is necessary to use stronger surface active agents, i.e. ionic surface active agents to make the cell wall of microbes permeable for small molecules. The ionic surfactants are selected by their specific properties, such as the length of alkyl chain, degree of ethoxylation (lipophily or hydrophility) and presence of radicals, such as quaternary salts, to affect the permeability of the cell wall of microbial cells for releasing nucleotides. Since many ionic surfactants precipitate proteins and inactivate enzymes, it is necessary to use a surfactant that does not inactivate the luciferase enzyme or other enzymes used in the bioluminescent reaction, or the reaction conditions have to arranged to such that the interference from the surfactant can be eliminated, e.g. by dilution.

The sample preparation for releasing nucleotides from a suspension of somatic or microbial cells require only the mixing of the surfactant in a concentration of from about 0.02 to 0.5% by volume of the total combined volumes of the sample suspension and surface active agent. The diffusion of metabolites from the cells through the membrane is so rapid that even ATP, which has a turnover time in the metabolism within the cell of less than one second, can be quantitatively released.

Bioluminescence is an extremely sensitive and specific analytical method of assaying nucleotides, but its utilization has been hampered by the lack of easy and reliable methods for extracting nucleotides. The present invention has been developed for simplifying and assuring reproducible and quantitative extraction of FMN, and purine and pyrimidine nucleotides from suspension of mono- and bilayers of somatic and microbial cells. The principles of the measurements are described below:

Bioluminescent measurement of ATP and other purine nucleotides

The theory of firefly bioluminescence and the measurement of ATP have been described in the literature and also in patents (U.S. Pat. No. 3,745,090). In this luminescent system ATP reacts with luciferase enzyme and luciferin substrate in the presence of magnesium catalyst and molecular oxygen-producing photons in the yellow-green range of the visible light spectrum. The photon efficiency of the reaction is 88%. Since photons can be counted down to a few photons per second, this reaction offers an extremely sensitive method of assaying ATP. By utilization of enzymatic conversion of other substrates of the 220 known ATP-specific enzymes to ATP it is possible to measure a large number of other nucleotides and substrates with this bioluminescent system at equally high sensitivity. With purified luciferase enzyme the reaction is specific to ATP; thus other nucleotides do not interfere with the measurement, so long as there are no enzymes in the sample to convert other nucleotides to ATP.

Examples of other nucleotides and substrates measurable through ATP are:

Guanosine phosphates, cytosine phosphates, inosine phosphates, uridine phosphates, thymidine phosphates and xanthosine phosphates by converting these with phosphotransferylase enzymes to ATP; adenosine diphosphate by converting it with pyruvate kinase to ATP; other nucleotide phosphates, such as pyruvate, glycero-, fructose, glucose, creatine, acetyl-, etc. phosphates and other substrates, such as nicotinamide mononucleotide and acetyl-Coenzyme A by converting these to ATP with appropriate kinase enzymes; acetate, adenosine monophosphate, cholin, creatine, glucose, fructose, pyruvate and other substrates through hydrolysis of ATP by appropriate kinase enzymes. Preferred reagents for bioluminescent assay of ATP contain:

|  | Range | Optimum |
| --- | --- | --- |
| Luciferase enzyme, purified from firefly light organs, | 0.1–20μg/ml | 1–5μg/ml |
| Luciferin synthetic or, purified from fireflies | 1–100μg/ml | 10–50μg/ml |
| Bovine serum albumin | 0.1–10mg/ml | 1–3mg/ml |
| Dithiothreitol | 10–200μg/ml | 100–200μg/ml |
| EDTA (ethylene diamine tetraacetic acid) | 0.1–1mg/ml | 0.2–0.5mg/ml |
| Magnesium salt (sulphate or acetate) and | 5–25mmolar | 5–10mmolar |
| Biochemical buffer, pH 7–8 (tris, HEPES, MOPS, etc.) | 10–100mmolar | 25–50mmolar |

Optimum pH for the reaction is 7.75, but in special applications a lower pH range can be beneficial.

Bioluminescent measurement of FMN and pyridine nucleotides

A bacterial bioluminescent system is the second most important bioluminescent reaction utilized for analytical purposes. The principles and the reaction components are described in literature. The reaction is also a luciferin-luciferase system as illustrated below:

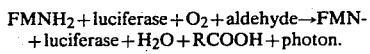
FMNH$_2$+luciferase+O$_2$+aldehyde→FMN-
+luciferase+H$_2$O+RCOOH+photon.

This reaction uses a reduced form of FMN as a luciferin and requires a long-chain aldehyde with more than eight carbons as a substrate. The photo efficiency of the reaction is 10%. The pH optimum is around 7.0 and the photons have a lambda maximum of 495 nm. This reaction can be used for measurement of the FMN level or number of bacteria based on the FMN assay in bacterial cells.

Before the measurement, the FMN is converted to the reduced form (FMNH$_2$) by chemical reducing agents, such as sodium dithionite.

The bacterial bioluminescent reaction can also be used for the assay of the reduced forms of nicotinamide adenine dinucleotide (NADH) and its phosphate (NADPH) through a coupled enzymatic reaction as photobacteria have two specific oxidoreductases for reducing FMN in the presence of NADH and NADPH:

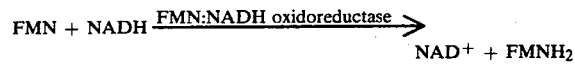
FMN + NADH $\xrightarrow{\text{FMN:NADH oxidoreductase}}$ NAD$^+$ + FMNH$_2$ A similar reaction can be used to convert FMN to FMNH$_2$ in the presence of NADPH with the FMN:NADPH oxidoreductase enzyme. The quantity of FMNH$_2$ produced and assayed with the bacterial bioluminescent reaction gives the equivalent quantity of reduced pyridine nucleotide (NADH or NADPH) in the sample.

Oxidized forms of pyridine nucleotides (NAD and NADP) can also be assayed with this system by converting these to reduced forms with appropriate dehydrogenase enzymes, such as lactate dehydrogenase for NADH and glucose-6- phosphate dehydrogenase for NADPH prior to the bioluminescent assay.

The reagents for the bacterial bioluminescent system contain the following:
For measuring of FMN,
  Bacterial luciferase, purified from photobacteria (Beneckea harveyi or Photobacterium species)
  Long-chain aldehyde 0.1% (decanal, dodecanal or tetradecanal)
  Dithiothreitol 1 mmolar
  Phosphate buffer, 0.1 molar, pH 6.9.
For Assaying NADH and NADPH,
  Bacterial luciferase
  FMN 5-20 nanomoles/ml
  FMN:NADH oxidoreductase (for NADH) or FMN:NADPH oxidoreductase (for NADPH)
  long-chain aldehyde 0.1%
  dithiothreitol 1 mmolar
  phosphate buffer, 0.1 molar, pH 6.9

The invention is further illustrated by the following examples of selective measurement of somatic and microbial cells:

1. Measurement of somatic cells

The enumeration of viable somatic cells is an important test in hematology for stored platelets and deep frozen red blood cells, in andrology for viability of spermatozoa and in the dairy field for diagnosing mastitis and testing the quality of raw milk by counting somatic cells. Somatic cells are counted now with electrical particle counters that detect the change in conductivity as cells pass through a narrow orifice, by direct microscopic counting, or by particle counters based on detecting fluorescent bodies. Particle counters are expensive and they do not distinguish between cells and other particles, such as dust, and they have no means of detecting viable cells from dead ones. Direct microscopic counting is subjective, time-consuming and inaccurate in determining the viability of cells.

Measurement of viability of somatic cells with the bioluminescent assay of ATP is both rapid and objective, but until now the sample preparation methods have been too cumbersome to make this technique feasible. In the present invention the sample preparation is simplified and made reliable by the use of non-ionic surface active agents. Non-ionic surface active agents, particularly, an octyl phenoxy polyethoxyethanol by the trade name of Triton *X-100, have been used to rupture somatic cells to allow an ATPase enzyme to destroy somatic ATP prior to extraction of bacterial ATP for the bioluminescent assay (U.S. Pat. No. 3,745,090). However, it has not been suggested in earlier patents or literature that non-ionic surfactants could be used to extract somatic ATP for quantitative assaying of somatic ATP or viable somatic cells. Furthermore, those non-ionic surfactants, such as Triton X100,

*Registered Trade Mark of Rohm and Haas Co., Philadelphia, Pa., USA. saponins and sulfosuccinates do not extract ATP instantaneously. A gradual extraction causes breakdown of ATP in the cells and erroneously low levels of ATP per viable cell. These types of detergents also are claimed to rupture the somatic cells, which means that the enzymes of the cells are also extracted and capable of hydrolyzing extracted ATP in the sample. This also leads to low ATP levels and irreproducibility. Furthermore, this type of non-ionic surfactant causes a partial inhibition of the bioluminescent reaction; saponins causing the highest inhibition and Triton X-100 the lowest, by about 25%.

The present invention applies non-ionic surface active agents for instantaneous and quantitative extraction of ATP from somatic cells in suspension or in a mono- and bilayer form. The extraction is based on the action of the non-ionic surfactant on the permeability of the cell membrane. The surfactant makes the membrane permeable to small size molecules which diffuse out of the cell towards the lower concentration gradient. The diffusion proceeds until the concentration of the small molecules is equal inside and outside the cells. Enzymes having a large molecular size cannot penetrate the small holes in the lipid layer of the membrane; thus enzymes remain inside the cells. Since the volume of the cells in the sample is usually less than 1%, small molecules, including the nucleotides and substrates, released over 99% to the extracellular solution. Non-ionic surfactants used for extraction of nucleotides from somatic cells are selected to provide quantitative release of nucleotides and not to inhibit luciferase enzymes. Therefore, the enzymes in the cells are not inhibited either. The molecules of nucleotides remaining in the cells after the equilibrium is established in the sample, subsequent to treatment with proper non-ionic surfactants, will be susceptible to enzymatic breakdown. Nucleotides in the sample are stable for about five minutes. A longer period between the release of nucleotides and the assay will cause errors because the cells' own enzymes lower the concentration of nucleotides inside the cells, and the nucleotides outside the cells start diffusing back into cells, towards the lower concentration gradient. If samples should be stored longer than a few minutes after releasing of nucleotides, they should be kept on ice, or the cells have to be removed by filtration or centrifuging.

The non-ionic surface active agents that make the cell membrane of somatic cells permeable for small molecules, but not for enzymes, and which do not have an inhibition on the bioluminescent reaction include ethoxylated alkylphenols having, e.g. the formula:

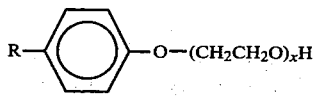

wherein R is an alkyl group having from 6 to 12 carbon atoms and x is from 2 to 20, and fatty acid polyglycol ethers having, e.g. the formula:

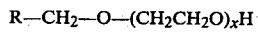

where x is 2–20 and R an alkyl group or fatty acid derivative having a 6 to 15 carbon atom chain.

These non-ionic surfactants are used in concentrations of 0.02–0.5% of the volume of the treated sample suspension. Their efficiency of releasing nucleotides from somatic cells is not effected by a pH between pH 2.0 and 12.0 if the nucleotide itself is not affected by acidity or alkalinity. Certain nucleotides, such as the reduced forms of pyridine nucleotides, NADH and NADPH, have to be extracted with a non-ionic surfactant having a pH of 8.5–12.0 in order to keep them stable. The oxidized forms of these nucleotides, NAD and NADP, are destroyed in alkaline solutions; thus they have to be extracted with a non-ionic surfactant at a pH below 4.0. At low pH the reduced forms, NADH and NADPH, are destroyed. It is thus possible to selectively release the oxidized and reduced forms of the pyridine nucleotides. Other nucleotides, such as the purine nucleotide phosphates (e.g. ATP, ADP, AMP, GTP GMP) can be released from cells in neutral pH, and in general they are not affected by the pH. Non-ionic surface active agents can be adjusted to desired pH with an acid, such as sulfuric, hydrochloric, nitric and acetic acid, or with a base, such as sodium, potassium and lithium hydroxide.

In order to assure rapid and quantitative release of nucleotides, the number of somatic cells should be less than ten million and preferably less than one million per milliliter.

Measurement of ATP in leucocytes in raw milk:

The efficiency of the release of nucleotides from somatic cells was tested with the bioluminescent ATP assay of somatic cells in raw milk. The extraction of ATP with a non-ionic surfactant (ethoxylated alkylphenol) was compared to two commonly used conventional extraction methods, i.e. the perchloric acid and the boiling tris-EDTA buffer methods.

The extraction procedures were:
A. Non-ionic surfactant method 1 ml 0.2% non-ionic surfactant (ethoxylated alkylphenol) in aqueous solution was added to 1 ml of raw milk and mixed for 15 seconds by shaking.
B. Tris-EDTA method 1 ml of milk was pipetted to 9 ml of boiling 20 mmolar tris (tris-hydroxy-methyl aminomethane) containing 2 mmolar EDTA, pH 7.4. Sample was boiled for 3 minutes and cooled on ice.
C. Perchloric acid method 0.1 ml 1 N perchloric acid was added to 1 ml of milk and solution mixed for one minute. Sample was neutralized by 0.1 ml 1 N sodium hydroxide.

Measurement of ATP was performed with a photon counter having a two-inch photomultiplier by pipetting 0.1 ml aliquotes to a transparent glass cuvette and injecting 0.1 ml luciferin-luciferase reagent into the sample in the instrument just prior to the measurement. The emitted light intensity was integrated over 10 seconds and the results read on a digital display as relative light units. The number of relative light units correlate directly to the concentration of ATP in the sample. However, due to different absorption of light in the sample and possible inhibitory substances in the sample, an internal standardization procedure (standard addition) has to be used to convert relative light units to ATP.

Results of the three methods are given below as a mean of triplicates:

|  | A Non-ionic surfactant sample | B Tris-EDTA sample | C Perchloric acid sample |
| --- | --- | --- | --- |
| Relative light units | 55,300 | 36,200 | 1,480 |

When the relative light units were converted to ATP by internal standardization, the non-ionic surfactant sample and Tris-EDTA sample had equal values when calculated per milliliter of milk, but the perchloric acid sample had only about 10% of the value of the two other methods.

In a study (Tarkkanen, P., R. Driesch and H. Greiling. A rapid enzymatic micromethod for the determination of intracellular and extracellular ATP and its clinical-chemical applications. Fresenius Z. Anal. Chem. 290:180, 1978) on different extraction methods of ATP from blood cells the non-ionic surfactant reagent (NRS*, Nucleotide Releasing Reagent for Somatic Cells) was compared to boiling tris and ethanol-EDTA extraction methods. Extraction with NRS was rapid and quantitative giving 96.8–102.2% yield and a correlation coefficient r+0.92–0.93 to the two other methods. The NRS method was simpler, more rapid and reproducible than the two other methods. Furthermore, NRS does not release ATP from microbial cells while the other methods do.

*Reg. Trade Mark of Lumac Systems AG, Basel, Switzerland.

Non-ionic surface active agents, such as ethoxylated alkylphenols do not inactivate luciferase enzymes, thus it is possible to prepare a single reagent for ATP measurement that contains the luciferin-luciferase reagents. The buffer and the nucleotide releasing reagent. This kind of a single reagent that extracts ATP and provides the bioluminescent reagents makes the use of the bioluminescent technique easy for field use and automation.

The extraction of nucleotides with ethoxylated alkylphenols and other suitable non-ionic surfactants from somatic cells provides several advantages over conventional methods: manipulations are simple, reagents are non-hazardous, methods are rapid and versatile (pH, temperature, field use, automation), samples are not diluted by the reagents and reagents are economical. The reagents have other uses besides the nucleotide measurements with bioluminescent systems as the permeability of cell membranes allows the measurement of enzyme activities in the cells without extracting the enzymes. In such applications substrates are added to the sample after membranes are made permeable with a non-ionic surfactant, and the conversion of the added substrate by the enzyme can be assayed.

2. Measurement of samples having a majority of microbial cells:

Samples having primarily microbial cells, e.g. activated sludge and microbial cultures, can be extracted for nucleotides without prior elimination of nucleotides of non-microbial cells. Microbial cell walls have substances, such as peptidoglycans, chitin and mucoidal substances that make the wall resistant to chemicals. Therefore, it is more difficult to release nucleotides from microbial cells than from somatic cells. According to the present invention, the application of ionic surface active agents changes the permeability of the cell wall and membrane of microbes to make them permeable for small size molecules, such as nucleotides, but not for enzymes. By "ionic surface active agents" is meant anionic or cationic surface active agents to the exclusion of non-ionic surface active agents. This selective permeability is obtaind by treating microbes with ionic surface active agents, the best of which are those that contain quaternary ammonium salts and a fatty group with a chain length of 12 carbon atoms. However, any chain length of carbon atoms from 8 to 18 can be used.

Examples of suitable ionic surfactants for quantitative release of nucleotides from microbial cells for bioluminescent measurement with firefly and photobacterial systems are: ethoxylated amines, ethoxylated diamines, polyethylene glycol esters of fatty acids, and ethoxylated amides having a chemical structure of

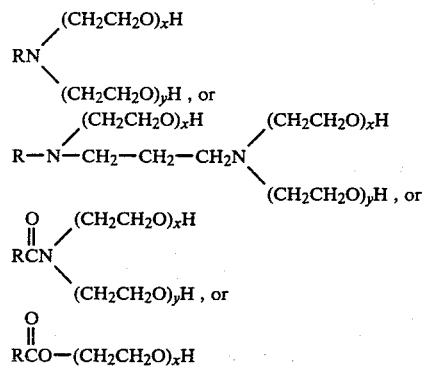

where R is a fatty alkyl group having 8–18 carbon atoms and x, y and z are numbers ranging from 2 to 50, and quaternary ammonium salts having a formula of

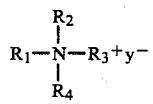

where $R_1$ and $R_2$ are an alkyl, alkyl-aryl-alkyl, ethoxyalkyl, hydroxyalkyl, or ethoxylated alkylphenol with a 4 to 22 carbon atom chain and the ethoxylated alkyls having 2 to 15 ethoxyl groups, and $R_3$ and $R_4$ are alkyl groups having a 1 to 15 carbon atom chain and y, e.g. a halogen, sulphate, sulphite or phosphate.

Combinations of the aforesaid amines and quaternary ammonium salts are particularly advantageous, since such combinations facilitate a precise release rate for the nucleotides.

Such surface active agents also include hyamine chloride, i.e. diisobutyl cresoxy epoxy ethyl dimethyl ammonium chloride.

Ethoxylated amines release nucleotides quantitatively from microbes, but the quaternary ammonium salts of ethoxylated amines penetrate the cell wall of microbes faster and quaternary salts are affected less by buffers, pH and other agents possibly encountered in the sample than are ethoxylated amines. A 0.02–0.5% solution of a mixture of 1 to 19 parts of an ethoxylated amine, and 1 to 19 parts of a quaternary ammonium salt of an ethoxylated amine both having a carbon atom chain length from 8 to 18, provides a complete and rapid release of nucleotides from bacteria, yeasts, fungi and slime molds as well as from certain bluegreen, green, brown and red algae. Nucleotides are also released from somatic cells with these reagents, but due to the precipitation of some proteins by the reagents, the release can be incomplete. These reagents do not inhibit firefly luciferase in the degree that it would interfere with the measurement. On the contrary, the presence of a low concentration of a quaternary ethoxylated amine (0.001–0.03%) enhances the turnover rate of the firefly luciferase and produces up to twice as many photons per second during the first part of the reaction as is produced by the same concentration of ATP with the same luciferin-luciferase reagents in plain buffer solution.

The rate of release of ATP and the bioluminescent reaction are affected by the proportions of the ethoxylated amine and the quaternary salt of the ethoxylated amine. The release of ATP and other nucleotides from microbial cells is slow, but still quantitative, and the reaction rate of luciferase the same as in buffer when ethoxylated amines are used for the release. By including a quaternary salt of an ethoxylated amine with the ethoxylated amine the rate of nucleotide release and the bioluminescent reaction can be increased from moderately slow to moderately fast depending on the proportion of the quaternary ethoxylated amine in the reagent.

The accompanying FIGURE illustrates the effect of the proportion of quaternary ethoxylated amine on the reaction kinetics and level of light emulsion as a function of time after adding ionic surface active agent in bacterial sample. Numbers refer to the percentage of ethoxylated amine and quarternary ethoxylated amine, respectively in a total concentration of 0.1% in the sample. Both had a chain length of 12 carbons. A refers to the time of adding the surface active agent and B to the time of adding the firefly reagent. In the tests 100 μl of 0.2% aqueous solution of the ethoxylated amine and a quaternary ethoxylated amine were pipetted to 100 μl volume of bacterial suspension (E. coli) and the sample was mixed by shaking for fifteen seconds before being measured in a photometer where 100 μl of luciferin-luciferase reagent was injected to the sample in a light-tight reaction chamber just prior to the measurement. The ethoxylated amine alone releases ATP from bacteria in 15 seconds and produces the same reaction kinetics as ATP in plain buffer, that is a continuous emission of light that decays 1 to 10% per minute depending on the proportions of the components in the luciferin-luciferase reagent. The quaternary salt of an ethoxylated amine used alone causes too fast a reaction rate to allow easy and reproducible measurement of ATP. A mixture of the ethoxylated amine and a quaternary salt of an ethoxylated amine, having both a 12 carbon chain length, gives the possibility to select a desired rate of nucleotide release and reaction kinetics. As can be seen in the FIGURE, the level of light emission is increased about two times by the use quaternary salt over the ethoxylated amine alone as a releasing agent. More than one half of a quaternary salt of an ethoxylated amine in the reagent causes inactivation of the luciferase enzyme; thus the proportions have to be controlled.

While ethoxylated amines do release nucleotides reasonably rapidly from bacteria, they produce a slow release from yeasts and fungi which have an even stronger cell wall than bacteria. Therefore, it is beneficial to include a quaternary salt of an ethoxylated amine as part of the release reagent. One third of a quaternary ethoxylated amine and two thirds of ethoxylated amine give a complete release of nucleotides, such as ATP and FMN from most bacteria in a few seconds, and from Mycobacteria, yeasts and fungi in 30–60 seconds.

Measurement of microbial cells

If the sample contains microbial cells only, or if the proportion of non-microbial cells is insignificant (activated sludge, soil, sediments) the release of nucleotides from the sample is accomplished by simply adding, e.g. a mixture of an ethoxylated amine and a quaternary ethoxylated amine in an end-concentration of 0.05–0.5% by volume of the sample. The reagent and sample are mixed and the reagent is allowed to remain in contact with the cells for a sufficient time to complete the release of nucleotides. After this the sample should be measured within five minutes to avoid any breakdown of nucleotides by the enzymes left inside the cells. These ionic reagents do inactivate some enzymes, among which is photobacterial luciferase. Therefore, the sample should be diluted 5 to 100 times after treatment and before measurement if FMN or pyridine nucleotides are measured in the sample with the bacterial bioluminescent system. The nucleotide release reagent for microbial cells, consisting of ethoxylated amines, can be adjusted to acidic and alkaline pH, thus the reduced and oxidized pyridine nucleotides can selectively be extracted from microbial cells.

The release reagent for microbial nucleotides requires a direct contact with the cell wall, in order to give a quantitative release. Therefore, the cells have to be in suspension. If cells form clumps or flocculates in the sample, they should preferably be dispersed prior to application of the reagent. The dispersion or homogenizing must not stress the cells because it would affect the level of nucleotides in the cells.

The table below shows that a linear relationship is obtained between the number of bacterial cells and the concentration of released ATP when a 3:7 mixture of an ethoxylated quaternary amine and ethoxylated amine were used to extract this purine nucleotide from E. coli suspension. The procedure was as follows:

100 μl of 0.2% releasing reagent was added to 100 μl of sample and the solution was mixed for 15 seconds. The sample was placed in the light-tight reaction chamber of the photon counter. Just prior to starting a 10-second integration, 100 μl of firefly luciferin-luciferase reagent was added to the sample in a transparent cuvette in the reaction chamber.

| Number of bacteria per milliliter | Relative light units for 10-second intergration |
|---|---|
| 150,000 | 1,480 |
| 500,000 | 4,800 |
| 1,000,000 | 9,580 |
| 2,000,000 | 18,900 |

The bacteria were grown on a liquid nutrient medium and the number of cells was determined by standard colony counting. The different dilutions were made in physiological saline solution.

The extraction efficiency of the release reagent based on a quaternary ethoxylated amine and an ethoxylated amine mixture was also tested against the boiling tris-EDTA buffer and the perchloric acid extraction methods. The samples consisted of whole blood diluted with physiological saline 200 times, suspension of E. coli bacteria in concentration of one million cells per milliliter, and a suspension of green algea, Chlorella sp.

Sample treatments were:
Ionic surface active nucleotide releasing reagent

To a 100 μl aliquot of sample solution, 100 μl of a 0.2% aqueous solution of a 3:7 part mixture of an ethoxylated quaternary amine and ethoxylated amine was pipetted and mixed for 15 seconds (for blood and bacteria) or 60 seconds (for algae);

Perchloric acid method 0.1 ml 1 N perchloric acid was pipetted to 1 ml of sample and mixed for one minute. Sample was neutralized by adding 0.1 ml 1 N NaOH;

Boiling tris-EDTA method

Nine milliliters of tris (0.02 molar)-EDTA (0.002 molar) at pH 7.4 was heated to boiling and 1 ml of sample solution was pipetted on the boiling buffer. Samples were boiled for three minutes and cooled on ice.

Measurement of ATP by bioluminescence

100 μl aliquots of extracted sample solution were pipetted into transparent glass cuvettes and these were placed into the light-tight reaction chamber of a photon counter. Just prior to the measurement, 100 μl of firefly luciferin-luciferase reagent was injected into the sample. The light emission was integrated for 10 seconds and the results read on the digital display as relative light units. The relative light units were converted to ATP by internal standardization whereby a known quantity of ATP standard was added into an aliquote of the extracted sample and measured as above. The standard was added in 10 μl in order not to change the total volume of the sample significantly. By subtracting the reading of the sample from that of the sample+added ATP standard a conversion factor for relative light units to ATP was calculated. The results of the extraction efficiency test are given below:

| Sample | Ionic surface active nucleotide releasing reagent | Perchloric acid method | Tris-EDTA boiling buffer |
|---|---|---|---|
| Whole blood | 100% | 7% | 80% |
| E. coli suspension | 100% | 3% | 95% |
| Chlorella sp., alga | 100% | — | 100% |

In all sample types the ionic surface active reagent gave the highest extraction efficiency. Boiling tris-EDTA buffer method extracted the same quantity of ATP from algae, but less from bacteria and blood. The low values obtained with perchloric acid method are due to coprecipitation of ATP with the perchlorate during the neutralization step. Perchloric ion is also a strong inhibitor of the firefly bioluminescent reaction.

3. Measurement of microbial cells in the presence of somatic cells

Measurement of bacteria in the presence of a large number of somatic cells can be performed by the measurement of FMN by the photobacterial bioluminescent system without significant interference from non-microbial FMN as somatic cells do not contain as much FMN as bacterial and other microbial cells. However, the bioluminescent system of photobacteria have only one tenth of the photon efficiency as the firefly bioluminescent system. Because of the high sensitivity of the bioluminescent assay of ATP and the high level of ATP in microbial cells, this bioluminescent system has been an attractive possibility for rapid detection and enumeration of microbial cells in body fluids, foodstuff and water. There has been only one big problem in the application of this method to body fluids and food samples—the high level of nonmicrobial ATP in such samples. The present invention offers great improvements to the preparation of this type of sample.

In earlier methods of measuring bacteria with the bioluminescent assay of ATP in body fluids and food samples somatic cells were ruptured with a non-ionic surfactant, Triton X-100 to get somatic ATP into solution, whereafter this ATP was hydrolyzed by an added ATPase enzyme, called apyrase (U.S. Pat. No. 3,745,090). Apyrase was inactivated after a 5–20 minute incubation by boiling, mineral acids, organic solvents or other chemicals. Boiling tris-EDTA buffer, nitric, sulphuric and perchloric acids have been used, simultaneously to inactivate apyrase enzyme and extract bacterial ATP. This method works in general, but it can cause large error due to incomplete elimination of non-bacterial ATP. The disadvantages of this method are:

Triton X-100 does not make all non-bacterial ATP available for apyrase because several studies report significant levels of residual non-bacterial ATP being found after the extraction of bacterial ATP in the sample (Conn, R. B., P. Charache and E. W. Chappelle. Limits of applicability of the firefly luminescence ATP assay for detection of bacteria in clinical specimens. Am. J. Clin. Path. 63:493-501, 1975.). It is also known that Triton X-100 extracts ATP from gram-positive bacteria and may cause errors if samples contain specimens, such as Streptococci. Triton also causes about 25% inhibition on the luciferase enzyme.

It appears that the greatest source of error in the Triton X-100/apyrase method is the fact that Triton does not disrupt all cells if the sample contains pieces of tissues, and it can be that proteins and fragments of somatic cells entrap part of somatic ATP so that it is not available for hydrolysis by the apyrase enzyme. Boiling in buffer and strong chemicals, such as mineral acids, are capable of solubilizing ATP from tissues and residual ATP from cell fragments.

The present invention promotes improved release of somatic ATP with the non-ionic surfactant, ethoxylated alkylphenol. After the release, somatic ATP can be eliminated by filtering, centrifuging or hydrolyzing with the apyrase enzyme (a $Ca^{++}$-activated ATPase enzyme from potatoes). After the elimination of somatic ATP, bacterial (or microbial) ATP is released with ionic surfactants, e.g. a mixture of an ethoxylated quaternary amine and ethoxylated amine. The treatment with these ionic surfactants, is not as radical as boiling or treatment with mineral acids; thus possible residual ATP in tissue particles is not released and does not cause errors. Since the non-ionic surfactants, e.g. ethoxylated alkylphenols, release ATP quantitatively from single somatic cells and monolayers of cells, such as pieces of epitelial tissue, there is no somatic ATP left to be released by the nucleotide releasing reagent consisting of ethoxylated amines. This new sample treatment method is both simpler and more accurate than the previously used methods for samples having both somatic and microbial cells.

A. Elimination of non-microbial ATP by filtration

An aliquot of sample containing both somatic and microbial cells is treated with a non-ionic surfactant, such as ethoxylated alkylphenol in an end concentration of 0.03–0.5% by volume of treated cell suspension. After a minimum of a 30-second waiting period a 0.1–10 ml sample is filtered through a membrane filter of the pore size of 0.2–0.45 μm for bacteria, 5 μm for yeast cells, or 20 μm for fungi. The filter is washed with sufficient volume of water, saline or buffer solution to remove any traces of released somatic ATP. The filter membrane contains now somatic cells that have no ATP and microbial cells unaffected by the nonionic surfactant. It is important not to have the microbial cells affected by too high a vacuum or dryness during the filtration because these stress the cells and their ATP level can drop to less than one half.

The filter is placed on the bottom of a flat-bottom measuring cuvette and the filter membrane is treated with a small volume of a solution containing 0.05–0.5% by volume of a mixture of an ethoxylated quaternary amine and an ethoxylated amine to release microbial ATP. After a 15–60 second mixing period, an aliquot of the solution can be assayed for microbial ATP by the bioluminescent assay.

An alternative method of releasing the microbial ATP is to pipette the ionic surfactant solution consisting of the mentioned ethoxylated amines directly on the filter after the filtration and washing step. When the microbial cell walls and membranes are made permeable for small molecules by the nucleotide releasing reagent (ethoxylated amines) microbial ATP diffuses out of the cells and can be pulled through the filter in the solution directly into the measuring cuvette for subsequent measurement with the bioluminescent reagents in photometer.

The filtering methods have the advantages that they eliminate somatic ATP, concentrate the sample, and eliminate any so-called quenching factors (colour, turbidity, and inhibitors of the luminescent reaction). The filtering methods can also be used to eliminate FMN and other nucleotides and substrates from somatic cells prior to measuring these in microbial cells.

B. Elimination of non-microbial ATP by centrifuging

An aliquot of sample, 0.1–10 ml, is treated with a non-ionic surfactant, e.g. ethoxylated alkylphenol in an end concentration of 0.03–0.5% by volume. After centrifuging at 5,000 to 20,000 g for 5 to 20 minutes, the supernate with the released non-microbial ATP is discarded. The centrifuge tube with the microbial sample is washed from residual traces of non-microbial ATP by resuspending microbial and somatic cells in 0.1–10 ml water, saline or buffer, and centrifuging the sample once more at 5,000 to 20,000 g for 5 to 20 minutes. After the centrifuging, the supernatant is discarded and a sufficient volume, 0.1–1 ml of 0.05–0.5% ionic surfactant, such as a mixture of an ethoxylated quaternary amine and an ethoxylated amine is pipetted into the centrifuge tube. After 15–60 seconds, microbial ATP is quantitatively released through the cell walls and membranes. An aliquot of the sample is pipetted into a measuring cuvette, and ATP is assayed by the firefly bioluminescent system by injecting the luciferin-luciferase reagent into the cuvette in the light-tight reaction chamber of the photometer.

The centrifuging method has the same advantages as the filtration method in eliminating non-microbial ATP, reducing quenching and concentrating the sample. The centrifuging method can also be used to eliminate FMN and other nucleotides and substrates from somatic cells prior to measuring these in microbial cells.

C. Elimination of non-microbial ATP with enzymatic hydrolysis

As described in U.S. Pat. No. 3,745,090 non-microbial ATP in solution can be eliminated by hydrolyzing it with an ATPase such as the apyrase enzyme which is a $Ca^{++}$-activated ATPase enzyme enzyme/from potatoes. This ATPase is used for this purpose due to its low price. The method given in the U.S. Pat. No. 3,745,090 applies apyrase enzyme in solution in such a high activity that the enzyme has to be inactivated (denaturated) prior to extracting microbial ATP. The denaturing step is performed simultaneously with the extraction of microbial ATP by methods, such as boiling tris-EDTA buffer and mineral acids. These radical procedures can lead to extraction of residual, non-microbial ATP that is contained by tissue particles and fragments of somatic cells. Furthermore, these treatments dilute the samples, thus lowering the overall sensitivity of the assay system.

With the present invention it is possible to improve the hydrolizing of non-microbial ATP more efficiently and without having to inactivate the apyrase enzyme. Two different alternatives are described below:

Hydrolysis of non-microbial ATP by a low activity of ATPase enzyme

Giving sufficient incubation time, a low activity of an ATPase enzyme, such as potato apyrase, can hydrolyze the quantity of non-microbial ATP found in body fluids and most food items. When the ATPase activity is low, it is possible to release and measure microbial ATP without having to inactivate the ATPase enzyme by heat or strong chemicals. Based on this principle a simple sample treatment method was developed for body fluids and food samples.

To an aliquot, 0.1–50 ml, of sample suspension a non-ionic surfactant, e.g. ethoxylated alkylphenol, in an end-concentration of 0.02–0.5% is added together with 0.01–0.2 units/ml, but preferably 0.03–0.1 units/ml, apyrase enzyme. The sample is incubated for 15 to 60 minutes at room temperature or at any temperature suitable for the microbial cells in the sample, but preferably between $+2°$ and $+40°$ C. The incubation time should be shorter than the generation time of the microbes in the sample at the incubation temperature, or the generation time should be known to allow the microbial cell count to be extrapolated back to time zero. During the incubation, somatic ATP is quantitatively released and hydrolyzed. After the incubation sample can be treated with ionic surfactants, e.g. a mixture of an ethoxylated quaternary amine and an ethoxylated amine, at an end-concentration of 0.05–0.5% to release microbial ATP. After a 15–60 second mixing time, an aliquot of 0.1–1 ml of the sample solution is measured with the luciferin-luciferase reagent in a photometer. This method is simple and ideally suited for samples which are taken outside the laboratory and brought to the laboratory within 15 to 120 minutes, which is the case with urine samples and samples of raw milk. In these cases the nucleotide releasing reagent (nonionic surfactant) and ATPase enzyme can be added to the sample upon the sample taking. The required incubation and elimination of non-microbial ATP is already completed by the time the sample arrives at the laboratory; thus it can be measured immediately. The incubation time of 15 to 30 minutes is also easy to adapt to automated methods and this procedure, requiring only addition of three reagents into the sample, is ideal for automation.

If the time delay between the sampling and adding of the non-ionic surfactant/ATPase reagent is longer than two hours, it does not affect the sample adversely as long as the growth of microbes can be prevented, e.g. by a low temperature, or if the growth of microbes can be estimated.

Hydrolysis of non-microbial ATP by immobilized ATPase enzyme

Immobilization of enzymes is a widely used and well-known technique in bio-engineering and biochemistry. The advantages of immobilized enzymes are that they can be used over and over again, they are more stable than enzymes in solution, and they can be removed from the reaction mixture at any desired time. In bioluminescent assays immobilized luciferase enzymes have already been applied (Jablonski, E. and M. DeLuca. Proc. Nat'l Acad. Sci. U.S.A., 73:3848 1976). In spite of the fact that immobilized ATPase, such as the apyrase, would be of great help in the sample preparation of body fluids for microbial count with the bioluminescent assay of ATP, immobilized apyrase has not been suggested yet. Utilization of immobilized ATPase complements the selective measurement of microbial cells with the application of non-ionic surfactants (e.g. ethoxylated alkylphenol) for selective release of non-microbial ATP and the subsequent use of ionic surfactants, e.g. ethoxylated amines, for releasing microbial ATP. In the present invention a method of using immobilized ATPase enzyme gives an easy alternative for elimination of non-microbial ATP from samples containing both somatic and microbial cells. This method is described below:

Non-ionic surfactant (ethoxylated alkylphenol, octylphenyl or fatty acid polyglycol ester) is added to the sample solution in an end-concentration of 0.02–0.5%. Immobilized ATPase, e.g. potatoe apyrase, is inserted to the suspension in the form of immobilized on, e.g. nylon tubing or screen, or on the surface of polystyrene cuvette or on glass or synthetic polymer beads. The sample is agitated to allow the immobilized enzyme to get in contact with all ATP molecules released from the somatic cells in the sample. During a 5 to 20 minute incubation time all non-microbial and extracellular ATP is hydrolyzed by the immobilized ATPase. After removing the solid object(s) containing the immobilized ATPase, the microbial cells can be treated with a ionic surfactant, e.g. a mixture of an ethoxylated quaternary amine and an ethoxylated amine; ethoxylated diamine; polyethylene glycol ester of fatty acid; or an ethoxylated alcohol, in an end-concentration of 0.05–0.5% to release microbial ATP. An aliquot of 0.1–1 ml of the sample solution is mixed with the firefly luciferin-luciferase reagent and the light emission is measured in a photometer.

The advantages of immobilized ATPase enzyme are that the same enzyme can be used hundreds of times, it is easy to apply in right activity and it can be removed before extraction of microbial ATP.

pH of the releasing agent

The non-ionic and ionic surface active agents described in this invention can be used at any pH ranging from pH 0.1 to 13.5. When a nucleotide is not stable due to chemical or enzymatic reactions during the extraction treatment of the cells or when it is desired that the nucleotides be preserved for longer than 1 to 10 minutes in the extracted sample, the surface active agent used for extraction is preferably applied in a solution having a ph below about 3 for acidic extraction or above about ph 10 for alkaline extraction. The choice between alkaline and acidic extraction depends on the nucleotide to be assayed. If the nucleotide is chemically stable and is assayed in less than 5 minutes from the time of being released from the cells, a surfactant at neutral or near neutral pH can be used for the extraction.

The extraction efficiency of different nucleotides by means of alkaline and acidic surface active agents was tested by using the same conditions for the nucleotides release as given in the earlier examples on selective measurement of somatic and microbial nucleotides and the number of cells in this description, except that the pH of the solution of surfactant was adjusted between pH 0.1 and 3 with an acidic buffer, i.e. a malate buffer or with an acid, i.e. acetic, sulphuric or hydrochloric acid, or with an alkaline buffer, i.e. a glycine, phosphate, borate or carbonate buffer, or with a base, i.e. sodium, potassium or lithium hydroxide to a pH between 10 and 13.5.

In order to obtain the optimum pH for the particular bioluminescent or chemiluminescent system used for the measurement of the extracted nucleotide, the buffering capacity of the buffer in the luminescent reagent, or its pH, is adjusted to such that when the sample and the reagent are mixed, the pH of the reaction mixture is at or near the optimum pH of the luminescent system. It is also possible to adjust the pH of the sample to the optimum of the luminescent reaction with addition of a buffer, acid or base prior to the luminescent assay. A preferred condition is that where the luminescent reagents will adjust the pH in the mixture of the sample and reagents to the desired pH.

Examples of nucleotide extraction with alkaline surface active agents

Non-ionic surfactants of the types of ethoxylated alkylphenols, fatty alcohols and fatty acid polyglycol ethers were prepared in a 2-50 mM phosphate buffer ($NaH_2PO_4$-NaOH) or in a base at a pH between 10 and 13.5. The concentration of the surfactant in buffered aqueous solution was between 0.05 and 1.0% by volume. This solution was applied to the sample in sufficient volume to result in an end concentration of surfactant of 0.03-0.5% volume of the treated sample mixture.

The said solution was used to release ATP from physiological saline (0.15 M NaCl) diluted human blood. The extraction of ATP was complete as compared to perchloric acid (0.1 N) or boiling tris (0.025 M)—EDTA(2 mM) buffer extractions. Blood samples treated with the alkaline non-ionic surfactant retained constant ATP level over 3 hours at room temperature, which indicates that the high pH inactivates enzymes, and prevents ATP from being broken down by chemical, enzymatic or microbial degradation.

ATP is extracted quantitatively also from tissue samples with alkaline non-ionic surfactant by means of homogenizing the sample in 10 to 100 volumes of the said surfactant solution per volume of tissue sample. Homogenizing is performed with a rotating, grinding or cutting homogenizer, or by sonication. The surfactant releases ATP from the cells the surfaces of which are exposed to the surfactant while the high pH inactivates the enzymes in these cells.

Extraction of other nucleotides than ATP was tested by measuring the reduced pyridine nucleotides, NHDH and NADPH in samples of diluted full blood and homogenized tissue samples with the bacterial bioluminescence assay after these samples were extracted with the above-mentioned alkaline surface active agent solutions. The extraction was quantitative as compared to extraction with alkaline (0.5 N NaOH)—alcohol (in 50% ethanol). NADH and NADPH were stable in such samples while the oxidized forms of pyridine nucleotides, NAD and NADP were broken down by the high pH during the extraction.

The extraction of nucleotides with alkaline ionic surfactants from microbial cells was tested by applying a 0.1-1.0% solution of ethoxylated amines, mixtures of ethoxylated amines and their quaternary salts, ethoxylated amides, and hyamine chloride to a suspension of microbial cells in a volume ratio to give an end concentration from between 0.05-0.5% by volume of the sample reagent mixture. The pH of the surfactant solution was adjusted between 10 and 13.5 by means of 2-50 mM alkaline buffer (ie. phosphate, glycine, borate and carbonate) or with a base (i.e. sodium, potassium and lithium hydroxides).

The extraction of ATP by means of the said alkaline ionic surfactant solution was complete when applied to samples of microbial cells, such as suspensions of bacteria, yeast, fungi and activated sludge. The extracted ATP was stable over 3 hours at room temperature and longer at lower temperatures.

Examples of extraction of nucleotides with acidic surface active agents:

Low pH is preferred for extracting certain oxidized nucleotides which will break down in alkaline pH, or which will be reduced by enzymes at neutral pH. Examples of such nucleotides are the oxidized forms of pyridine nucleotides NAD and NADP, NADH and NADPH are broken down at acidic pH, and will not interfere in the assays. To test the extraction of these, 10-1000 ul of diluted full blood (10-100 times with physiological saline) was treated with 0.1-1.0% solution by volume of non-ionic surface active agents (ethoxylated alkylphenols, fatty alcohols and fatty acid polyglycol ethers having a pH between 0.1 and 3 adjusted with a buffer (i.e. malate) or with an acid (i.e. acetic, sulphuric and hydrochloric acid). The sample and the non-ionic surfactant are mixed in a volume of water to give a surfactant concentration between 0.02 to 0.5% in the total volume of sample and reagent mixture. NAD and NADP were quantitively extracted as compared to extraction with 0.5 N perchloric acid. The assays of NAD and NADP were performed by bacterial bioluminescence after the nucleotides were enzymatically converted to reduced forms, the former with malate dehydrogenase and the latter with glucose-6-phosphate dehydrogenase.

These examples illustrate that the surface active agents herein described, can be used at different pH ranges to obtain specific extraction of nucleotides either from somatic cells or microbial cells with non-ionic and ionic surfactants, respectively. The advantage of the extraction at low or high pH is that it is more specific (oxidized versus reduced forms) and that the extracted nucleotides are stable longer in the sample solution, which means that measurement thereof can be delayed for a considerable period of time, as much as about 2-3 hours.

The combination of methods for preparing samples of somatic and microbial cells disclosed in the invention makes it possible to measure the number of cells and the concentration of nucleotides and substrates selectively for somatic or microbial cells by bioluminescent systems of the firefly and photobacteria techniques. The sample preparation methods are easy, rapid and reliable, allowing them to be applied to routine tests in medical, industrial and hygiene laboratories.

The application of bioluminescent assay of ATP and FMN for enumerating microbial cells is based on the fact that the level of the nucleotides in cells is relatively constant. ATP levels in viable bacteria vary from 0.1 to 2 femtograms ($10-15$ g) per cell depending on the cell size, and the level of FMN from $0.6 \times 10^{-16}$ g to $2.2 \times 10^{-16}$ g per cell. Because of the higher sensitivity and the high level of ATP in bacteria, the bioluminescent assay of the firefly bioluminescent assay/of ATP has been preferred for rapid enumeration of microbial cells over the bacterial bioluminescent assay of FMN. For this reason the examples given in the descriptions of this invention are given in more detail for the ATP assay. This does not imply that the applications of the invention are less useful for assaying of other nucleotides than ATP. As can be seen in the examples, the modes of operation are also suitable for pyridine nucleotides and other substrates having a small molecular size.

The principles, preferred embodiments, examples and modes of operations of the present invention described in the foregoing specification are for illustrative purposes only and are not intended to restrict the invention which is to be limited solely to the scope of the claims hereinafter made.

What is claimed is:

1. A method for measuring the concentration of ATP in microbial cells and the member of viable microbial cells contained in a biological sample composed of a mixture of somatic and microbial cells, which comprises contacting said sample with a non-ionic surface active agent selected from the group consisting of ethoxylated alkyl phenols and fatty acid poly glycol ethers under conditions to selectively release ATP from essentially only the somatic cell without rupturing the cell membranes of the somatic cells, removing the somatic ATP thereby released, further contacting the sample with an ionic surface active agent selected from the group consisting of ethoxylated amines, ethoxylated diamines, ethoxylated amides, polyethylene glycol esthers of fatty acids, quaternary ammonium salts, and mixtures thereof under conditions to selectively release ATP from the microbial cells without rupture of the cell membranes and cell walls of the microbial cells, and thereafter measuring by means of a bioluminsecent assay technique the concentration of ATP selectively released from the microbial cells and thereby determining the number of viable microbial cells in the sample.

2. The method of claim 1, wherein the non-ionic, ethoxylated alkyl phenol surfactant is of the formula:

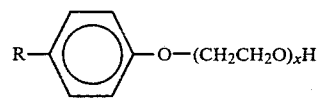

wherein R is an alkyl group having from 6 to 12 carbon atoms and x is from 2 to 20, and the non-ionic fatty acid polyglycol ethers are of the formula:

$$R-CH_2-O-(CH_2CH_2O)_xH$$

wherein R is an alkyl group having from 6 to 15 carbon atoms and x is from 2 to 20.

3. The method of claim 2, wherein the ionic surface active agents are of the following formalae:

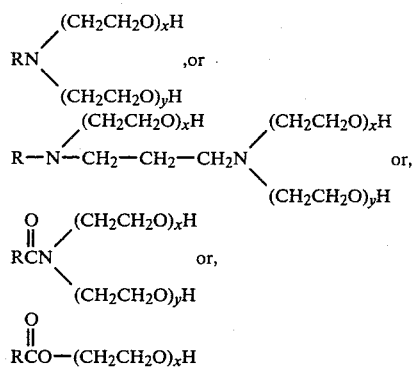

where R is a fatty alkyl group having 8-18 carbon atoms and x, y and z are numbers ranging from 2 to 50, and quaternary ammonium salts having a formula of

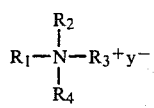

where $R_1$ and $R_2$ are an alkyl, alkyl-aryl-alkyl, ethoxyalkyl, hydroxyalkyl, or ethoxylated alkylphenol with a 4 to 22 carbon atom chain and the ethoxylated alkyls having 2 to 15 ethoxyl groups, and $R_3$ and $R_4$ are alkyl groups having a 1 to 15 carbon atom chain and y, is a halogen, sulphate, sulphite or phosphate.

4. A method according to claim 3, wherein the ionic surface active agent is diisobutyl cresoxy epoxy ethyl dimethyl ammonium chloride.

5. A method for measuring the concentration of ATP in microbial cells and the number of viable microbial cells contained in a biological sample composed of a mixture of somatic and microbial cells, which comprises contacting said sample with a nonionic surface active agent of the formula:

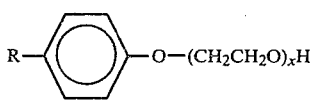

wherein R is an alkyl group having from 6 to 15 carbon atoms and x is from 2 to 20, under conditions to selectively release ATP from essentially only the somatic cells without rupturing the cell membranes of the somatic cells, removing the somatic ATP thereby released, further contacting the sample with a mixture of ionic surface active agents comprising a mixture of ethoxylated amine and a quaternary ammonium salt of an ethoxylated amine under conditions to selectively release ATP from the microbial cells without rupture of the cell membranes and cell walls of the microbial cells, and thereafter measuring by means of a bioluminescent assay technique the concentration of ATP selectively released from the microbial cells and thereby determining the number of viable microbial cells in the sample.

6. A method according to claim 5, wherein the measurement of ATP is performed by means of firefly bioluminescent measurement.

7. A method according to claim 5, wherein released ATP is measured within 5 minutes from treatment by firefly bioluminescent reagents containing 0.01-1 ug/ml luciferase enzyme, 1-100 ug/ml luciferin, 10-200 ug/ml dithiothreitol, 0.1-10 mg/ml bovine serum albumin, 5-50 mg/ml magnesium ion in a 10 to 100 millimolar biochemical buffer, at a ph from 6.5 to 8.5 in a photometer to detect photons between the wavelengths of 400 and 650 nanometers.

8. The method of claim 5 wherein ATP is released from the somatic cells by contacting a suspension, monolayer, or bilayer of the cells with the non-ionic surfactant in an amount of from about 0.02 to 0.5% by volume of the combined suspension, monolayer, or bilayer and the surfactant for about 5 to 15 seconds.

9. The method of claim 5, wherein ATP is released from bacterial, yeast, fungal and slime mold cells in suspension or monolayer by contacting the cells with the ionic surface active agent in an amount of from about 0.02 to 0.5% by volume of the combined suspension monolayer and the surfactant for about 10 to 60 seconds.

10. The method of claim 5 wherein the concentration of ATP released from the somatic cells is measured by firefly or bacterial bioluminescence assay techniques and the number of somatic cell in the sample is thereby determined.

11. The method of claim 5, wherein removed of ATP released from somatic cells and measuring of ATP in microbial cells is accomplished by
   a. centrifuging the sample, after the releasing of the somatic ATP with a non-ionic surfactant, at 5,000-20,000 g for 5 to 20 minutes,
   b. discarding the supernate containing somatic ATP,
   c. resuspending the cells in water, saline or buffer solution for the microbes in the sample,
   d. centrifuging the sample at 5,000-20,000 g for 5 to 20 minutes,
   e. discarding the supernate, and releasing the ATP from microbial cells in he centrifuge tube with a small volume of ionic surface active agent, and
   f. measuring the ATP concentrations by the firefly bioluminescent assay.

12. The method of claim 5, wherein the removal of ATP released from the somatic cells is accomplished by an enzymatic hydrolysis.

13. The method of claim 12, wherein removal of ATP released from somatic cells and measuring of ATP in microbial cells is accomplished by filtering the released somatic ATP through a 0.2-0.45 um membrane filter for bacterial samples, through a 5 um membrane for yeast samples and through a 20 um pore size membrane for fungal samples, and the ATP is released from microbial cells by treating the filter membrane with a volume of ionic surface active agent sufficient to release ATP, from the microbial cells on the filter and measuring the ATP concentration by firefly assay.

14. The method of claim 12, wherein the enzymatic hydrolysis is performed at a low, controlled activity of the enzyme by utilization of a 15 to 60 minute incubation time at temperatures between 2° C. and 45° C., the activity of the enzyme being so low that it does not have to be activated before releasing the ATP from microbial cells, the break-down of released microbial ATP being insignificant or the break-down magnitude being correctable based upon the time lag between the releasing of the ATP and the measurement thereof.

15. The method of claim 14 wherein the enzymatic hyrolysis of released ATP is from somatic cells is performed by an ATPase enzyme in an activity range of 0.01-0.2 international units per milliliter of sample, in the presence of 2 to 20 millimolar calcium ion at a pH between 4.0 and 8.5.

16. The method of claim 5, wherein the sample is contacted with the surface active agent at a pH of from about 0.1 to 3.0.

17. The method of claim 5, wherein the sample is contacted with the surface active agent at a pH of from about 10 to 13.5.

18. A method of measuring the concentration of ATP in microbial cells and the number of viable microbial cells contained in a biological sample containing predominantly microbial cells, comprising contacting the sample with a mixture of ionic surface active agents comprising an ethoxylated amine and a quaternary ammonium salt of an ethoxylated amine under conditions to selectively release ATP from the microbial cells without rupture of the cell membranes and cell walls of the microbial cells, and thereafter measuring by means of a firefly bioluminescent assay the concentration of ATP selectively released from the microbial cells and thereby determining the number of viable microbial cells in the sample.

* * * * *